United States Patent
Okano

(10) Patent No.: US 8,407,459 B2
(45) Date of Patent: Mar. 26, 2013

(54) INFORMATION PROCESSING APPARATUS AND BOOT COMPLETION NOTIFICATION PROGRAM

(75) Inventor: Kensuke Okano, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 90 days.

(21) Appl. No.: 13/064,593

(22) Filed: Apr. 1, 2011

(65) Prior Publication Data

US 2011/0185164 A1 Jul. 28, 2011

Related U.S. Application Data

(63) Continuation of application No. PCT/JP2008/068651, filed on Oct. 15, 2008.

(51) Int. Cl.
*G06F 15/177* (2006.01)
*G06F 9/00* (2006.01)
*G06F 11/00* (2006.01)

(52) U.S. Cl. .................. 713/2; 713/1; 714/2; 714/47.1

(58) Field of Classification Search ................ 713/1, 2; 714/2, 47.1
See application file for complete search history.

(56) References Cited

U.S. PATENT DOCUMENTS

| | | | |
|---|---|---|---|
| 6,442,699 B1 | 8/2002 | Nakajima | |
| 6,606,716 B1 * | 8/2003 | Vrhel et al. | 714/32 |
| 6,681,336 B1 | 1/2004 | Nakazato et al. | |
| 7,340,638 B2 * | 3/2008 | Nicholson et al. | 714/6.11 |
| 8,055,890 B2 * | 11/2011 | Yu et al. | 713/1 |
| 2002/0095619 A1 * | 7/2002 | Marsh | 714/23 |
| 2005/0168638 A1 | 8/2005 | Iwata | |
| 2005/0235294 A1 | 10/2005 | Kimura et al. | |
| 2006/0225038 A1 | 10/2006 | Okabe | |
| 2007/0203916 A1 | 8/2007 | Kwak | |

FOREIGN PATENT DOCUMENTS

| | | |
|---|---|---|
| EP | 0 990 977 | 4/2000 |
| JP | 60-089247 | 5/1985 |
| JP | 62-133549 | 6/1987 |
| JP | 4-171512 | 6/1992 |
| JP | 8-263320 | 10/1996 |
| JP | 10-243368 | 9/1998 |
| JP | 2000-155626 | 6/2000 |
| JP | 2000-222075 | 8/2000 |
| JP | 2001-005661 | 1/2001 |
| JP | 2004-171485 | 6/2004 |
| JP | 2005-217908 | 8/2005 |
| JP | 2005-284491 | 10/2005 |
| JP | 2005-309551 | 11/2005 |
| JP | 2006-070543 | 3/2006 |
| JP | 2006-195816 | 7/2006 |
| JP | 2006-259873 | 9/2006 |

(Continued)

OTHER PUBLICATIONS

Patent Abstracts of Japan, Publication No. 2006-259873, Published Sep. 28, 2006.

(Continued)

*Primary Examiner* — Stefan Stoynov
(74) *Attorney, Agent, or Firm* — Staas & Halsey LLP

(57) ABSTRACT

In an information processing apparatus, a stopwatch unit detects boot-up of an information processing apparatus, and measures as a boot time a time elapsed from the detection of the boot-up. A determination unit determines whether the boot time has reached notification timing. An output unit outputs a boot completion notification when the determination unit determines that the boot time has reached the notification timing indicated by boot completion notification timing information as a result of comparison therebetween.

10 Claims, 14 Drawing Sheets

FOREIGN PATENT DOCUMENTS

| | | |
|---|---|---|
| JP | 2006-350489 | 12/2006 |
| JP | 2007-219582 | 8/2007 |
| JP | 2007-234010 | 9/2007 |
| KR | 10-2007-0088959 | 8/2007 |
| WO | WO 2005/074264 | 8/2005 |

OTHER PUBLICATIONS

Patent Abstracts of Japan, Publication No. 10-243368, Published Sep. 11, 1998.
Patent Abstracts of Japan, Publication No. 2005-309551, Published Nov. 4, 2005.
Patent Abstracts of Japan, Publication No. 62-133549, Published Jun. 16, 1987.
Patent Abstracts of Japan, Publication No. 60-089247, Published May 20, 1985.
Patent Abstracts of Japan, Publication No. 4-171512, Published Jun. 18, 1992.
Patent Abstracts of Japan, Publication No. 2005-217908, Published Aug. 11, 2005.
Patent Abstracts of Japan, Publication No. 2000-222075, Published Aug. 11, 2000.
Patent Abstracts of Japan, Publication No. 2005-284491, Published Oct. 13, 2005.
Patent Abstracts of Japan, Publication No. 2006-350489, Published Dec. 28, 2006.
Patent Abstracts of Japan, Publication No. 2006-070543, Published Mar. 16, 2006.
Patent Abstracts of Japan, Publication No. 2007-234010, Published Sep. 13, 2007.
Patent Abstracts of Japan, Publication No. 2000-155626, Published Jun. 6, 2000.
Patent Abstracts of Japan, Publication No. 2007-219582, Published Aug. 30, 2007.
Patent Abstracts of Japan, Publication No. 2001-005661, Published Jan. 12, 2001.
Patent Abstracts of Japan, Publication No. 8-263320, Published Oct. 11, 1996.
Patent Abstracts of Japan, Publication No. 2006-195816, Published Jul. 27, 2006.
International Search Report for PCT/JP2008/068651, mailed Nov. 11, 2008.
Partial Translation of Japanese Reference No. 2005-284491, already of record.
Partial Translation of Japanese Reference No. 2000-222075, already of record.
Espacenet Bibliographic Data, Korean Reference No. 10-2007-0088959, published Aug. 30, 2007.
Korean Office Action issued Sep. 28, 2012 in corresponding Korean Patent Application No. 10-2011-7007053.
Patent Abstracts of Japan, Publication No. 2004-171485, Published Jun. 17, 2004.
Japanese Patent Office Action issued in Japanese Patent Application No. 2010-533748 dated Sep. 4, 2012.

* cited by examiner

151a  BOOT COMPLETION NOTIFICATION TIMING TABLE

| TIME DATA LABEL | NOTIFICATION TIMING |
|---|---|
| APPOINTED TIME | 340 |
| MEASUREMENT TIME 1 | 362 |
| MEASUREMENT TIME 2 | 357 |
| MEASUREMENT TIME 3 | 367 |
| MEASUREMENT TIME 4 | 378 |
| ⋮ | ⋮ |
| MEASUREMENT TIME 15 | 368 |

FIG. 4

INFORMATION PROCESSING APPARATUS AND BOOT COMPLETION NOTIFICATION PROGRAM

This application is a continuing application, filed under 35 U.S.C. §111(a), of International Application PCT/JP2008/068651, filed on Oct. 15, 2008.

FIELD

This invention relates to an information processing apparatus and boot completion notification program.

BACKGROUND

Conventionally, information processing apparatuses such as personal computers (Personal Computer: PC) may display a progress bar or the like to represent the startup status of a multitasking Operating System (Operating System: OS), an application program, or the like during the startup thereof.

Patent Literature 1: Japanese Laid-open Patent Publication No. 2006-259873
Patent Literature 2: Japanese Laid-open Patent Publication No. 10-243368
Patent Literature 3: Japanese Laid-open Patent Publication No. 2005-309551
Patent Literature 4: Japanese Laid-open Patent Publication No. 62-133549
Patent Literature 5: Japanese Laid-open Patent Publication No. 60-089247
Patent Literature 6: Japanese Laid-open Patent Publication No. 4-171512
Patent Literature 7: Japanese Laid-open Patent Publication No. 2005-217908

PROBLEMS THAT THE INVENTION IS TO SOLVE

In information processing apparatuses such as PCs, however, resident applications and/or services may start up simultaneously or successively even after an OS completes its startup. During the startup of them, an initialization process and so on still put load on a CPU and memories. Therefore, a user is not able to use the information processing apparatus comfortably until the startup is fully completed.

Further, conventionally, a boot status of an information processing apparatus is displayed based mainly on the startup progress of an intended program. The above-mentioned techniques make it possible to display a startup status of each application (whether the startup is now in progress or is complete). However, this status is not the one that informs the user whether or not the information processing apparatus has entirely completed its boot-up process and is now ready to use. Therefore, it is a problem that it is difficult for the user to confirm whether the boot-up of the information processing apparatus is complete or not.

There may be considered a technique of making a notification of boot completion of the information processing apparatus when a specified application such as an application or OS completes its startup. However, it is also a problem that this technique would not be flexible about a change in configuration caused by installment of a new application or the like.

SUMMARY

According to an aspect of the invention, an information processing apparatus includes: a storage unit that stores boot completion notification timing information indicating notification timing for making a boot completion notification that notifies a user that the information processing apparatus has completed boot-up and is now ready to use; a stopwatch unit that detects the boot-up of the information processing apparatus, and measures as a boot time a time elapsed from the detection of the boot-up; a determination unit that determines whether the boot time measured by the stopwatch unit has reached the notification timing indicated by the boot completion notification timing information; and an output unit that outputs the boot completion notification when the determination unit determines that the boot time has reached the notification timing.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 illustrates an example structure of a boot completion notification timing table.

DESCRIPTION OF EMBODIMENTS

A preferred embodiment of the present invention will be described in detail below with reference to the accompanying drawings.

Figure 1:
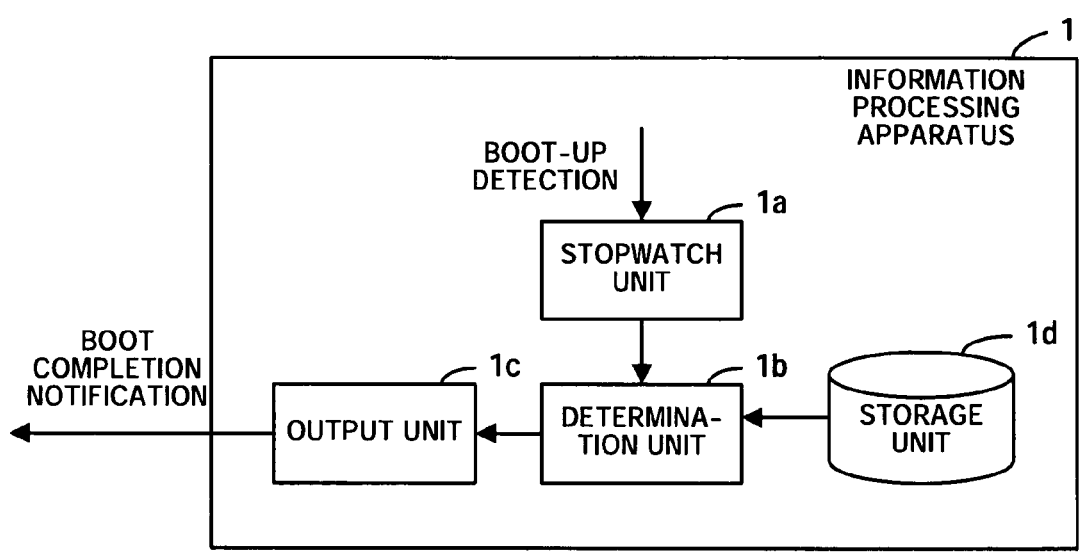
FIG. 1 outlines one embodiment.

FIG. 1 outlines one embodiment. An information processing apparatus 1 illustrated in FIG. 1 has a boot completion notification function of notifying a user of boot completion of the information processing apparatus 1. This information processing apparatus 1 includes a stopwatch unit 1a, a determination unit 1b, an output unit 1c, and a storage unit 1d.

The stopwatch unit 1a detects boot-up of the information processing apparatus 1, and measures, as a boot time, a time elapsed from the detection of the boot-up of the information processing apparatus 1.

The determination unit 1b determines whether the boot time measured by the stopwatch unit 1a has reached notification timing indicated by boot completion notification timing information stored in the storage unit 1d. This boot completion notification timing information includes time information indicating notification timing. When the determination unit 1b determines that the boot time measured by the stopwatch unit 1a has reached the notification timing as a result of comparison therebetween, the output unit 1c outputs a boot completion notification.

The output unit 1c outputs the boot completion notification when the determination unit 1b determines that the boot time has reached the notification timing indicated by the boot completion notification timing information as a result of comparison therebetween. The boot completion notification output from this output unit 1c causes a display unit, not illustrated, to display a boot completion notification, so that the user confirms that the information processing apparatus 1 has completed its boot-up and runs stable and that the information processing apparatus 1 is now ready to use.

This display unit may be provided integrally with or separately from the information processing apparatus 1.

Further, the boot completion notification output from the output unit 1c may be stored in a computer or storage device, not illustrated. In this case, this stored boot completion notification is displayed or read as occasion arises.

The storage unit 1d stores the boot completion notification timing information indicating the notification timing for making a boot completion notification that notifies a user that the information processing apparatus 1 has completed its boot-up and is now ready to use.

In the information processing apparatus 1 described above, the storage unit 1d stores the boot completion notification timing information indicating notification timing. The stopwatch unit 1a detects boot-up of the information processing apparatus 1 and measures the boot time. The determination unit 1b determines whether the boot time has reached the notification timing. When the determination unit 1b determines that the boot time has reached the notification timing, the output unit 1c outputs the boot completion notification.

As described above, when the determination unit 1b determines that the boot time has reached the notification timing, the output unit 1c outputs the boot completion notification. That is, the user is notified of boot completion of the information processing apparatus 1 on the basis of the boot status of the information processing apparatus 1. Thereby, the user is able to confirm that the information processing apparatus 1 has completed its boot-up and runs stable and that the information processing apparatus 1 is now ready to use. As a result, the user is able to start to use the information processing apparatus 1 comfortably after boot-up.

The following describes one embodiment in detail with reference to the accompanying drawings.

Figure 2:
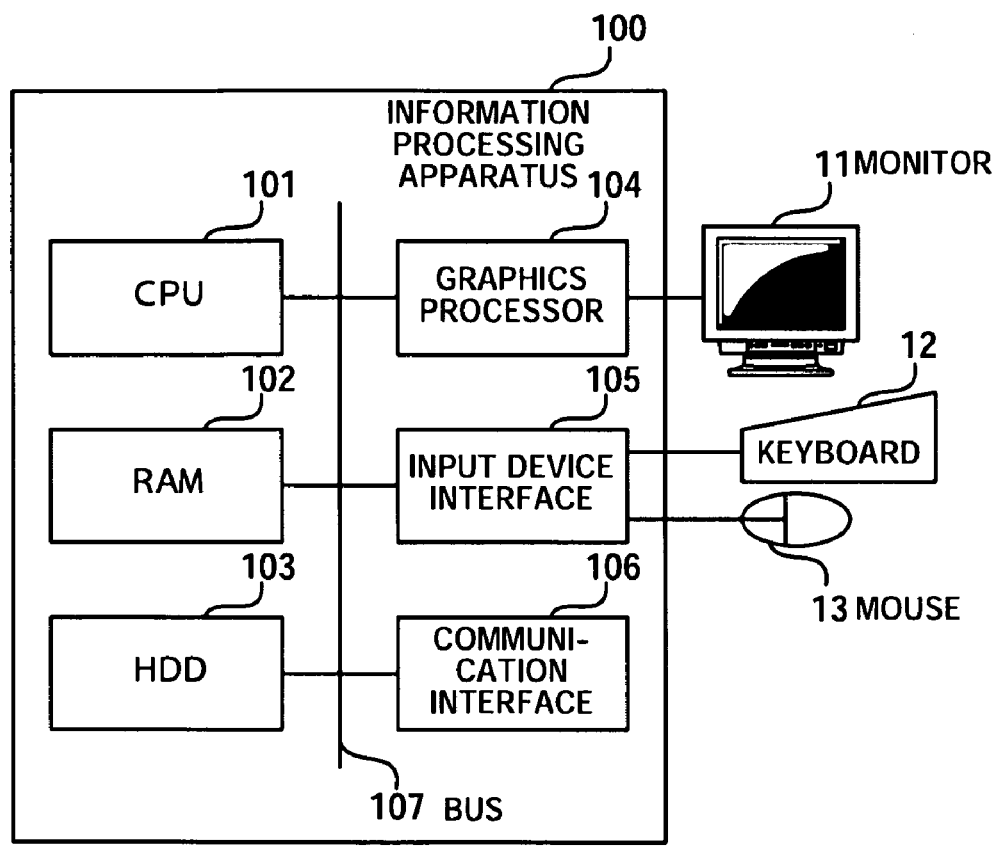
FIG. 2 illustrates a hardware configuration of an information processing apparatus.

FIG. 2 illustrates a hardware configuration of an information processing apparatus. The information processing apparatus 100 illustrated in FIG. 2 is entirely controlled by a CPU (Central Processing Unit) 101. Connected to the CPU 101 via a bus 107 are a RAM (Random Access Memory) 102, a hard disk drive (HDD: Hard Disk Drive) 103, a graphics processor 104, an input device interface 105, and a communication interface 106.

The RAM 102 temporarily stores at least part of an OS (Operating System) program and application programs to be executed by the CPU 101. This OS may be a multitasking OS. The RAM 102 also stores various kinds of data for processes to be performed by the CPU 101. The HDD 103 stores the OS and application programs.

The graphics processor 104 is connected to a monitor 11. This graphics processor 104 is designed to display images on a display of the monitor 11 under the control of the CPU 101. The input device interface 105 is connected to a keyboard 12 and a mouse 13. This input device interface 105 is designed to transfer signals from the keyboard 12 and mouse 13 to the CPU 101 via the bus 107.

The communication interface 106 is connectable to a network, not illustrated. This communication interface 106 is designed to communicate data with other computers via the network.

With the above-described hardware configuration, the processing functions according to this embodiment are realized.

Figure 3:
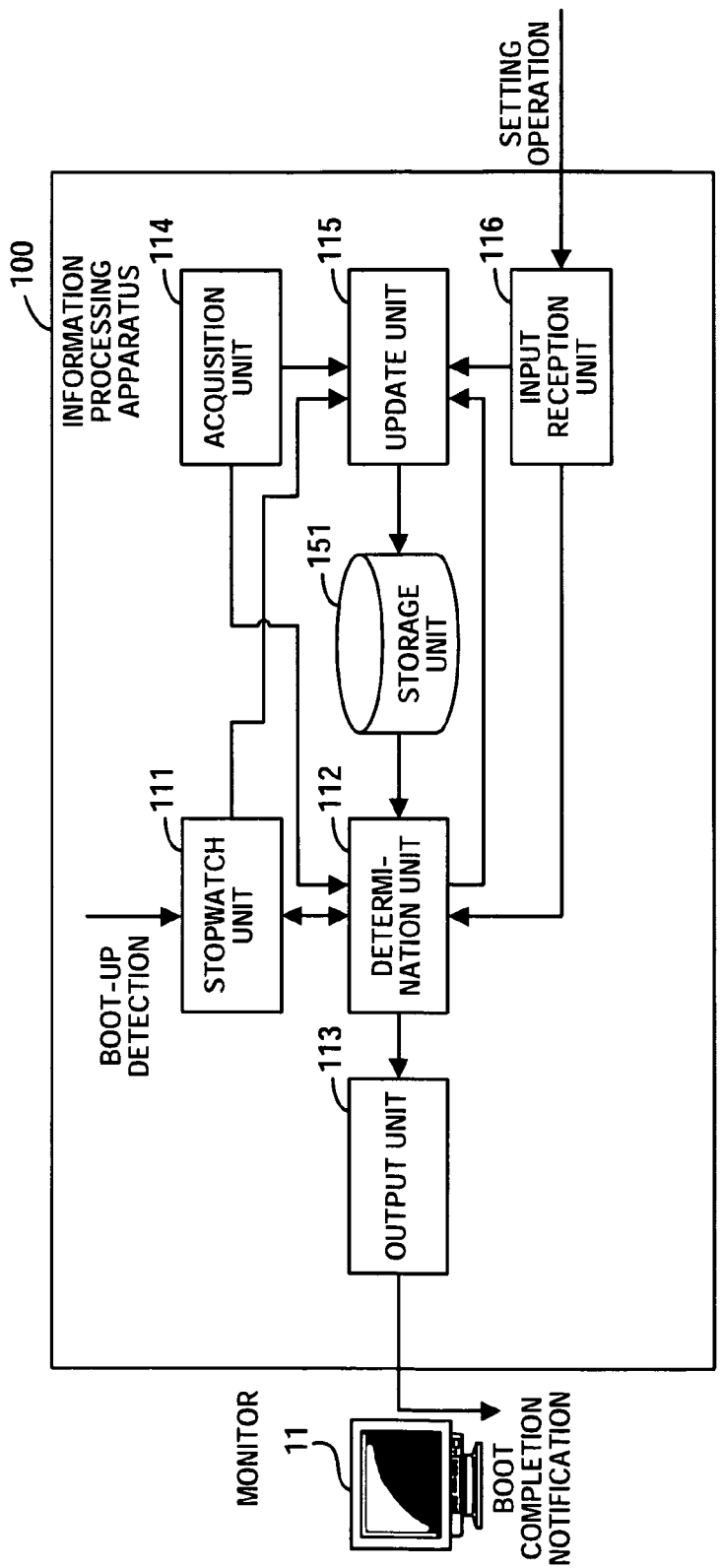
FIG. 3 is a block diagram illustrating a configuration of an information processing apparatus.

FIG. 3 is a block diagram illustrating a configuration of an information processing apparatus. The information processing apparatus 100 illustrated in FIG. 3 is a personal computer that needs some time to get ready to use after starting boot-up because the boot-up process puts load on a CPU, and has a boot completion notification function of notifying a user of boot completion of the information processing apparatus 100. The information processing apparatus 100 includes a stopwatch unit 111, a determination unit 112, an output unit 113, an acquisition unit 114, an update unit 115, an input reception unit 116, and a storage unit 151. In addition, the information processing apparatus 100 is connected to a monitor 11.

The stopwatch unit 111 detects boot-up of the information processing apparatus 100, and measures, as a boot time, a time elapsed after the detection of the boot-up of the information processing apparatus 100.

The determination unit 112 determines whether the boot time measured by the stopwatch unit 111 has reached notification timing indicated by boot completion notification timing information stored in the storage unit 151. This boot completion notification timing information includes time information indicating the notification timing. When the determination unit 112 determines that the boot time measured by the stopwatch unit 111 has reached the notification timing indicated by the time information included in the boot completion notification timing information, as a result of comparison therebetween, the output unit 113 outputs a boot completion notification.

In addition, the determination unit 112 determines based on load conditions acquired by the acquisition unit 114 whether the information processing apparatus 100 has completed its boot-up. More specifically, the determination unit 112 determines that the information processing apparatus 100 has completed its boot-up when values indicating the load conditions acquired by the acquisition unit 114 are equal to or lower than predetermined values.

To enhance reliability of this determination, the determination unit 112 repeatedly determines whether the load conditions acquired by the acquisition unit 114 meet predetermined criteria (whether or not the values indicating the load conditions acquired by the acquisition unit 114 are equal to or lower than the predetermined values), until the completion of the boot-up is confirmed. Then, the determination unit 112 determines that the information processing apparatus 100 has completed its boot-up when the determination result that the load conditions meet the predetermined criteria is obtained a predetermined number of times in a row.

Based on the determination of the determination unit 112 on the load conditions indicating the load imposed on the information processing apparatus 100 on boot-up (the load includes all load on the information processing apparatus 100 and mainly on the CPU 101), the update unit 115 updates the boot completion notification timing information, as will be described in detail later with reference to FIGS. 8 to 12.

According to user setting, the output unit 113 is caused to output a boot completion notification on the basis of the determination of the determination unit 112 on the load conditions of the information processing apparatus 100 on boot-up, instead of the determination based on comparison between boot time and notification timing, as will be described in detail later with reference to FIGS. 11 and 12.

Figure 14:
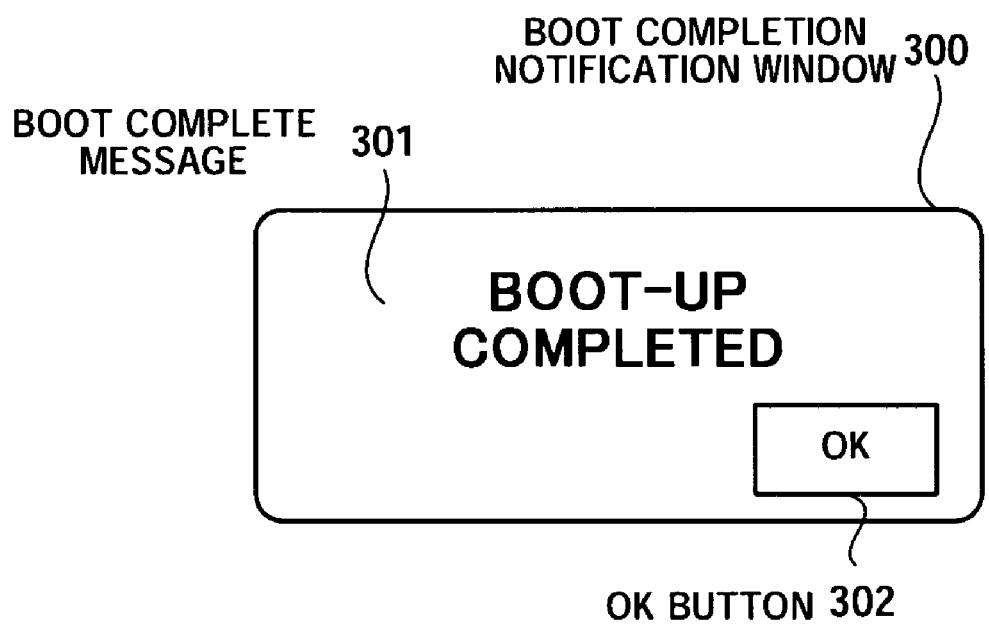
FIG. 14 illustrates a boot completion notification window.

When the determination unit 112 determines that the boot time has reached the notification timing indicated by the boot completion notification timing information as a result of comparison therebetween, the output unit 113 outputs a boot completion notification, as will be described in detail later with reference to FIG. 14. More specifically, the output unit 113 outputs boot completion notification display information, for example, for displaying a boot completion notification window as shown in FIG. 14 on the monitor 11.

The boot completion notification output from the output unit 113 displays a boot completion notification on a display device such as the monitor 11, so that the user is able to confirm that the information processing apparatus 100 has completed its boot-up and runs stable and that the information processing apparatus 100 is now ready to use.

Similarly to the monitor 11, the display device for displaying the boot completion notification may be provided integrally with or separately from the information processing apparatus 100.

Further, the boot completion notification is not limited to those displayed on the display device. Alternatively, output of a voice message of "boot-up is now complete" or the like, output of a specified sound signal, lightning of a light emitting device such as a ramp, or another method may be employed as long as they notify a user of boot completion of the information processing apparatus 100.

Still further, the boot completion notification output from the output unit 113 may be stored in another information processing apparatus or storage device, not illustrated, which is connected to the information processing apparatus 100 via an electric communication line. In this case, the stored boot completion notification is displayed or read as occasion arises.

The acquisition unit 114 acquires the load conditions of the information processing device 100 on boot-up. As the load conditions of the information processing device 100 on boot-up, the acquisition unit 114 acquires the utilization of the CPU 101 (described earlier with reference to FIG. 2) of the information processing apparatus 100 and a rate of access to the HDD 103 (described earlier with reference to FIG. 2) of the information processing apparatus 100. As other kinds of load conditions, the acquisition unit 114 may acquire the utilization of the RAM 102 of the information processing apparatus 100, the size of page file usage, and the like.

The update unit 115 updates the boot completion notification timing information stored in the storage unit 151. More specifically, when the determination unit 112 determines that the information processing apparatus 100 has completed its boot-up, the update unit 115 acquires the boot time measured by the stopwatch unit 111, and stores boot completion notification timing information indicating the acquired boot time in the storage unit 151.

The input reception unit 116 receives appointed timing information set by a user and user inputs regarding the boot completion notification function of the information processing apparatus 100.

The storage unit 151 stores the boot completion notification timing information indicating notification timing for making a boot completion notification that notifies a user that the information processing apparatus 100 has completed its boot-up and is now ready to use.

Figure 5:
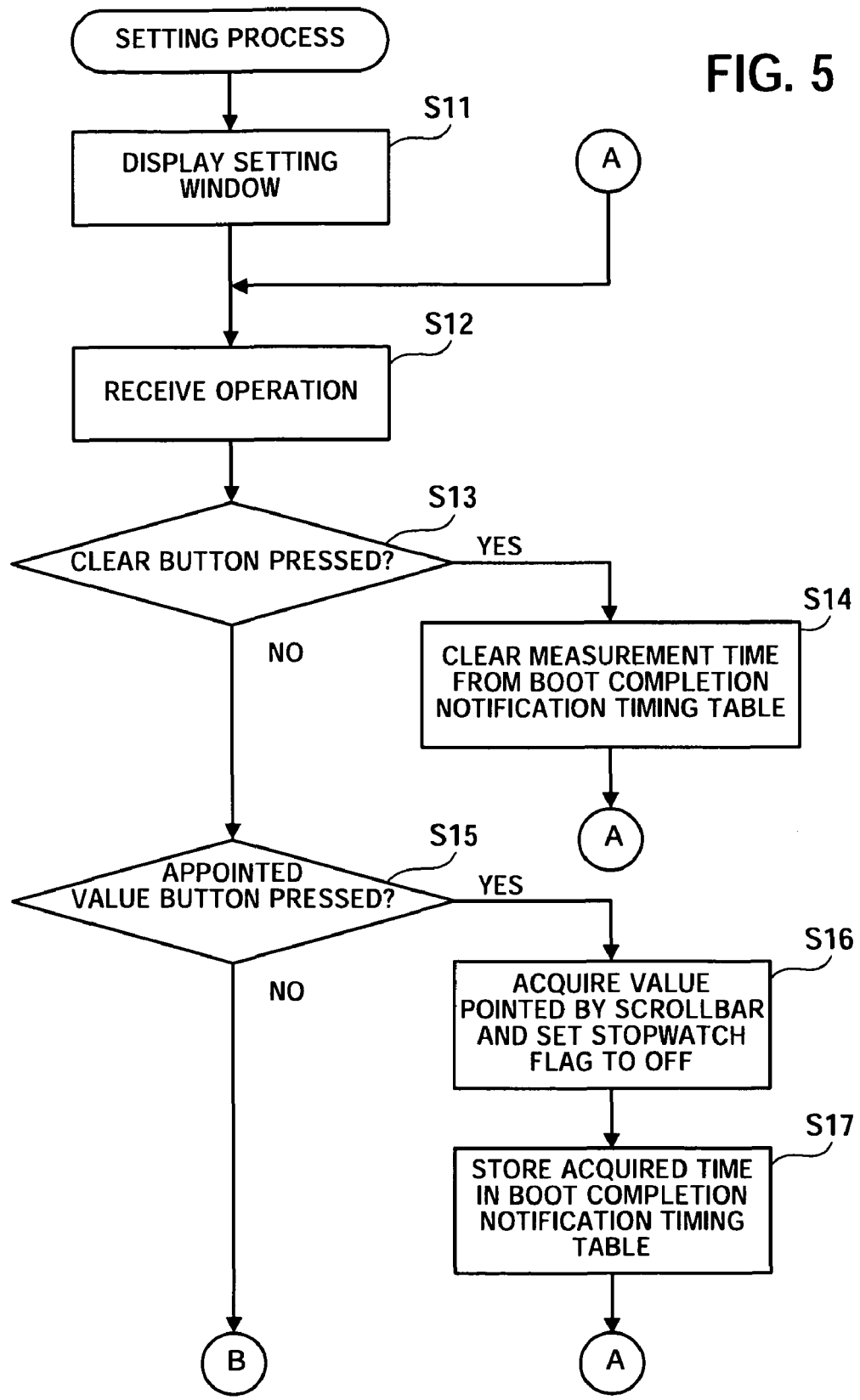
FIG. 5 is a flowchart of a setting process.
Figure 6:
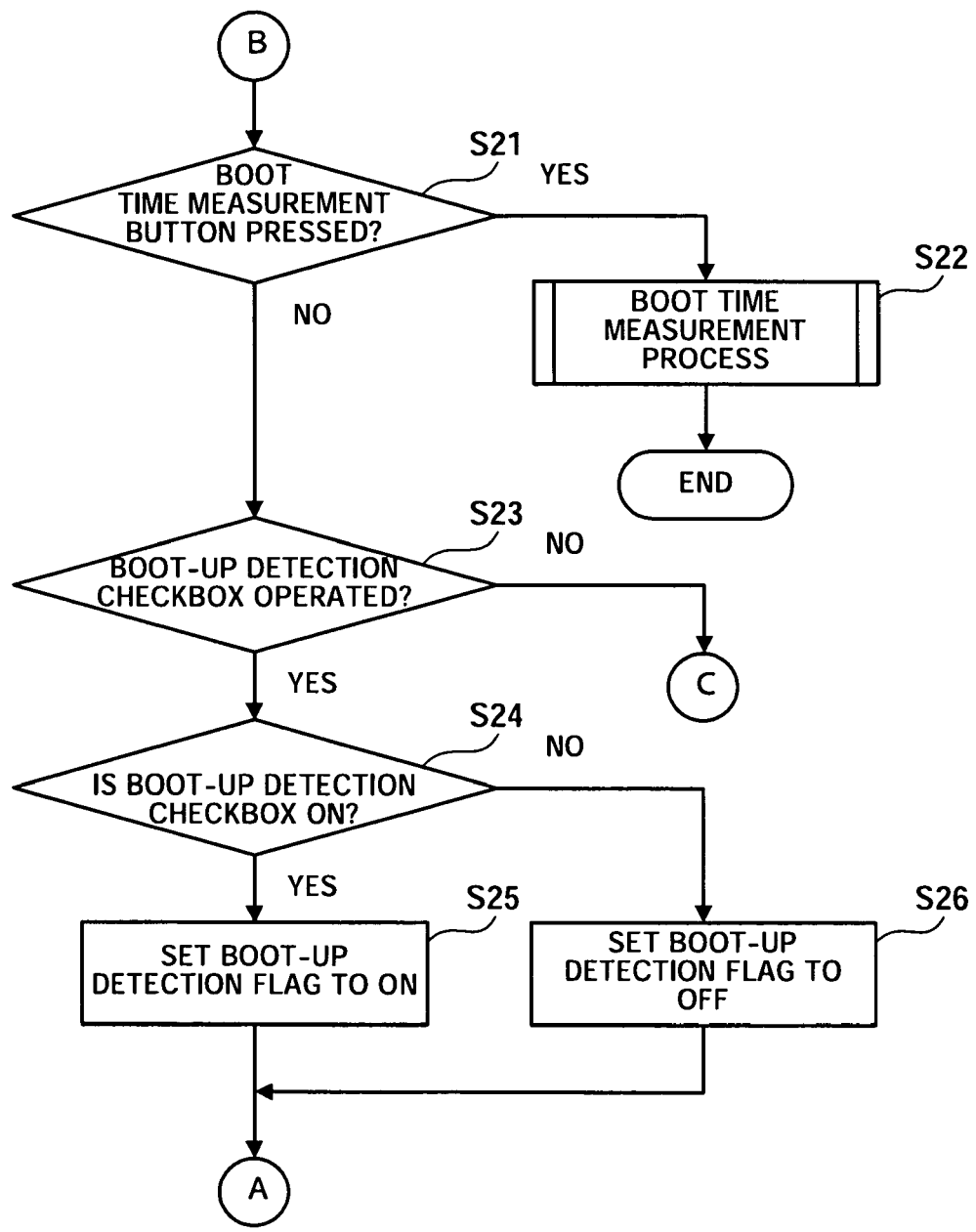
FIG. 6 is the flowchart of the setting process.
Figure 7:
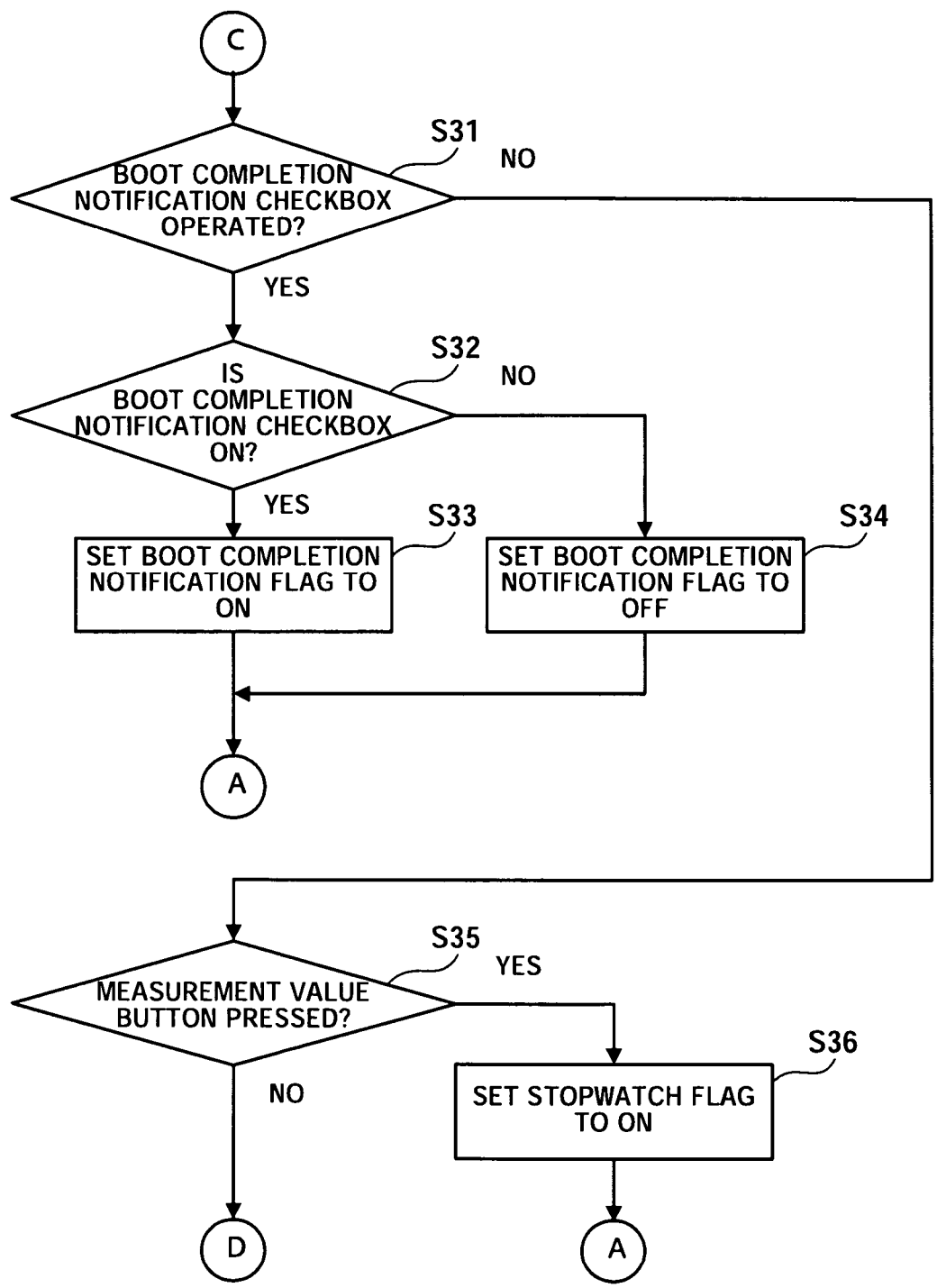
FIG. 7 is the flowchart of the setting process.
Figure 8:
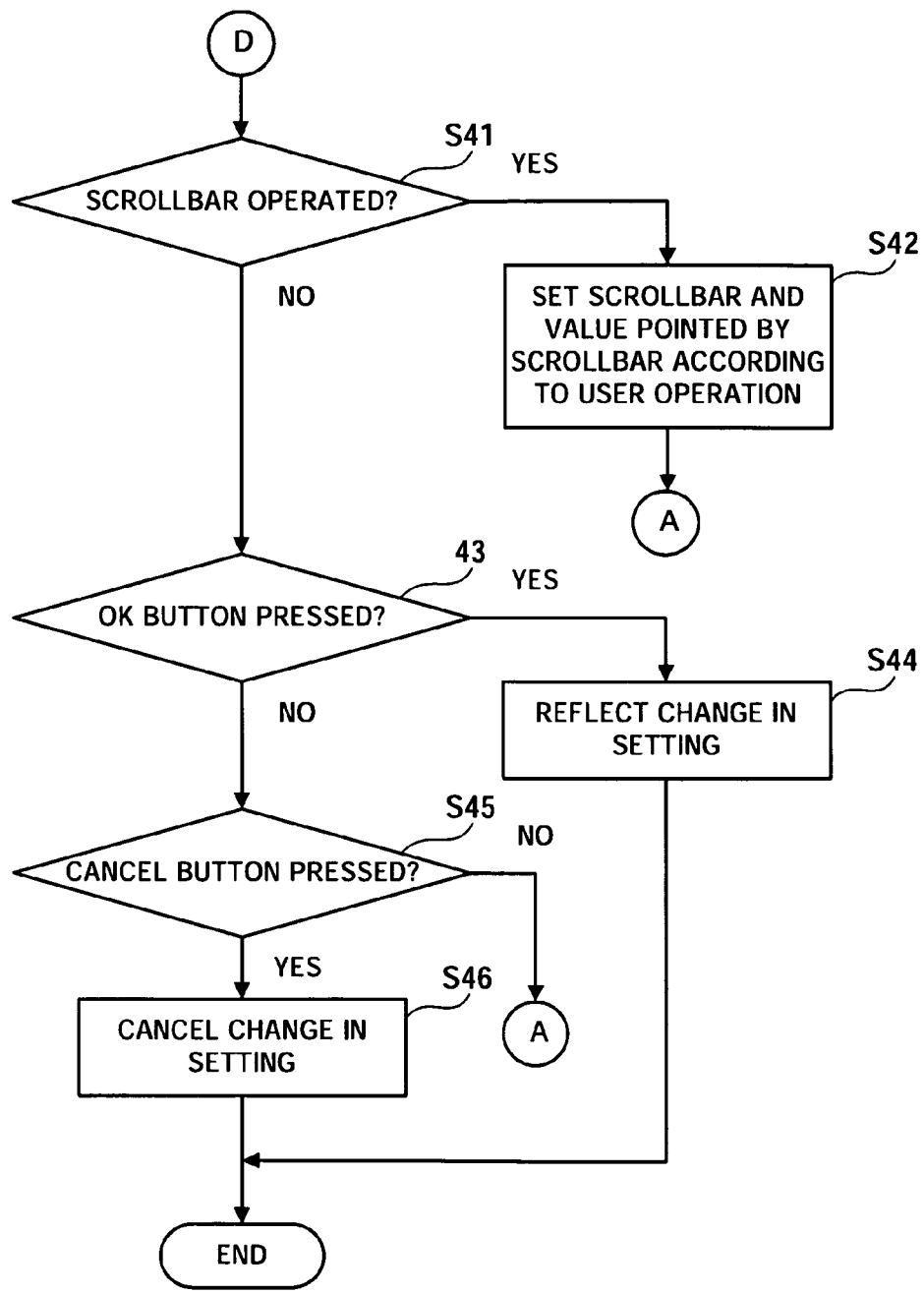
FIG. 8 is the flowchart of the setting process.

This boot completion notification timing information includes an appointed time that is appointed timing information indicating notification timing set by a user, as will be described in detail later with reference to FIG. 5. In addition, the boot completion notification timing information includes a measurement time that is timing information indicating a boot time measured in boot-up of the information processing apparatus 100.

This embodiment uses the information processing apparatus 100 that is a personal computer, by way of example, and is implemented with any other information processing apparatuses that need some time to get ready to use after starting its boot-up.

The following describes an example data structure of data that is used in this embodiment.

FIG. 4 illustrates an example structure of a boot completion notification timing table. The boot completion notification timing table 151a illustrated in FIG. 4 is created and managed by the information processing apparatus 100 (described earlier with reference to FIG. 2); and is stored in the HDD 103 (described earlier with reference to FIG. 2). The HDD 103 according to this embodiment functions as a storage unit 151. The boot completion notification timing table 151a is a table that stores boot completion notification timing information indicating timing for making a notification of boot completion of the information processing apparatus 100.

The boot completion notification timing table 151a has fields for "time data label" and "notification timing". The "time data label" field contains a label associated to the data contents of notification timing. The "notification timing" field indicates timing for making a notification of boot completion of the information processing apparatus 100. Data in fields arranged in a horizontal direction is associated with each other to form one piece of boot completion notification timing information.

An appointed time in the boot completion notification timing information is data that indicates timing set by a user for making a boot completion notification. This data will be described in detail later with reference to FIGS. 8 and 13.

A measurement time in the boot completion notification timing information is data that indicates a time measured from detection of boot-up of the information processing apparatus 100 until detection of completion of the boot-up. Regarding the boot completion notification timing information indicating a measurement time, a plurality (for example, 15 pieces) of data is stored in the boot completion notification timing table 151a, and a value obtained by averaging the measurement times indicated by the boot completion notification timing information is used as timing for making a boot completion notification.

In the boot completion notification timing information, the notification timing of the appointed time is a value set by a user in a setting process (to be described later with reference to FIGS. 5 to 8). The notification timings of the measurement times 1 to 15 are values obtained with a boot time measurement process (to be described later with reference to FIGS. 9 and 10). Out of the measurement times 1 to 15, the notification timing of measurement time 1 is the oldest value, that is, the value obtained first, the notification timing of measurement time 2 is the second oldest value, and the notification timing of measurement time 15 is the newest value, that is, the value obtained most recently.

In this connection, the boot completion notification timing table 151a has an upper limit for the number of boot completion notification timing information to store measurement times. When the boot completion notification timing table 151a containing the maximum number (15 pieces) of data is updated to store a new measurement time, the oldest data, i.e., the measurement time 1 is deleted, the notification timings of measurement times 2 to 15 are moved up by one to the notification timings of measurement times 1 to 14, respectively, and the new measurement time is stored as the notification timing of measurement time 15.

The boot completion notification timing table 151a according to this embodiment stores 15 pieces of boot completion notification timing information indicating measurement time. However, the number of information is not limited thereto, and 14 pieces or less, or 16 pieces or more may be stored.

In addition, the boot completion notification timing table 151a according to this embodiment has the upper limit for the number of boot completion notification timing information to store measurement times. Alternatively, without providing the upper limit, all obtained boot completion notification timing information is averaged, and the calculated value may be used as a reference for determining a boot status.

In the information processing apparatus 100 according to this embodiment, the boot completion notification timing information is generated in response to user input to the information processing apparatus 100 or by the information processing apparatus 100 collecting information at the time of boot-up, and is stored in the HDD 103.

The following describes processes to be performed in this embodiment.

FIGS. 5 to 8 are a flowchart of a setting process. The setting process of FIGS. 5 to 8 is performed for setting a boot completion notification function. This setting process is initiated by a user operating the keyboard 12, mouse 13, or the like.

(Step S11) The output unit 113 displays a setting window on a display screen of the monitor 11. This setting window is a window that allows a user to set the boot completion notification function, as will be described in detail later with reference to FIG. 13.

(Step S12) The input reception unit 116 receives user input made on the setting window that was displayed at step S11.

(Step S13) The input reception unit 116 determines whether a clear button has been pressed on the setting window. This clear button will be described in detail later with reference to FIG. 13. If the clear button has been pressed, the process proceeds to step S14. Otherwise, the process proceeds to step S15.

(Step S14) The update unit 115 clears (deletes) all measurement times from the boot completion notification timing table 151a described earlier with reference to FIG. 14.

In this embodiment, in this step S14, the measurement times are not actually cleared from the boot completion notification timing table 151a, but only an update instruction to clear the measurement times and the contents of the update are stored in the RAM 102. The update is actually done at step S44, as will be described later with reference to FIG. 8. That is to say, before step S44 is executed, it is possible to cancel this update by canceling the update instruction at step S46 to be described later with reference to FIG. 8, which results in canceling the setting process of this time with keeping the current setting.

(Step S15) The input reception unit 116 determines whether an appointed value button has been pressed on the setting window. This appointed value button will be described in detail later with reference to FIG. 13. If the appointed value button has been pressed, the process proceeds to step S16. Otherwise, the process proceeds to step S21 (to be described later with reference to FIG. 6).

(Step S16) The input reception unit 116 acquires a value pointed by a scrollbar displayed on the setting window. Then, the update unit 115 sets a stopwatch flag stored in the RAM 102 to OFF. This stopwatch flag is a flag to indicate whether to use an appointed time set by a user or a measurement time obtained with the boot time measurement process (to be described later with reference to FIG. 9) as notification timing for making a boot completion notification. This stopwatch flag is stored in the RAM 102.

(Step S17) The update unit 115 updates the appointed time in the boot completion notification timing table 151a, described earlier with reference to FIG. 4, according to the value pointed by the scrollbar, which was acquired at step S16. Then, the process proceeds to step S12.

According to the embodiment, similarly to step S14, in these steps S16 and S17, the update of the appointed time in the boot completion notification timing table 151a according to a value pointed by the scrollbar and the update of the stopwatch flag based on the user operation made on the appointed value button are not actually done, but only an update instruction to update the appointed time and the stopwatch flag and the contents of the update are stored in the RAM 102. The update is actually done at step S44, as will be described later with reference to FIG. 8. That is to say, before step S44 is executed, it is possible to cancel this update by canceling the update instruction at step S46 to be described later with reference to FIG. 8, which results in canceling the setting process of this time with keeping the current setting.

(Step S21) The input reception unit 116 determines whether a boot time measurement button has been pressed on the setting window. This boot time measurement button will be described in detail later with reference to FIG. 13. If the boot time measurement button has been pressed, the process proceeds to step S22. Otherwise, the process proceeds to step S23.

(Step S22) The update unit 115 executes the boot time measurement process. This boot time measurement process will be described in detail later with reference to FIGS. 9 and 10. Then, the process is completed.

(Step S23) The input reception unit 116 determines whether a boot-up detection checkbox has been operated on the setting window. This boot-up detection checkbox will be described in detail later with reference to FIG. 13. If the boot-up detection checkbox has been operated, the process goes on to step S24. Otherwise, the process goes on to step S31 (to be described later with reference to FIG. 7).

(Step S24) The input reception unit 116 determines whether the boot-up detection checkbox is ON (checked). If the boot-up detection checkbox is ON (this means that the user operation has changed this box from OFF to ON), the process goes on to step S25. If the boot-up detection checkbox is OFF (this means that the user operation has changed this box from ON to OFF), the process goes on to step S26.

(Step S25) The input reception unit 116 sets a boot-up detection flag to ON. Then, the process goes on to step S12 (described earlier with reference to FIG. 5). This boot-up detection flag is a flag that indicates whether to make a boot completion notification on the basis of the load on the information processing apparatus 100, and is stored in the RAM 102, as will be described in detail later with reference to FIG. 11.

(Step S26) The input reception unit 116 sets the boot-up detection flag to OFF. Then, the process goes on to step S12 (described earlier with reference to FIG. 5).

In this embodiment, similarly to step S14, in these steps S25 and S26, the update of the boot-up detection flag based on the user operation made on the boot-up detection checkbox is not actually done, but only an update instruction to update the boot-up detection flag and the contents of the update are stored in the RAM 102. The update is actually done at step S44, as will be described later with reference to FIG. 8. That is to say, before step S44 is executed, it is possible to cancel this update by canceling the update instruction at step S46 to be described later with reference to FIG. 8, which results in canceling the setting process of this time with keeping the current setting.

(Step S31) The input reception unit 116 determines whether a boot completion notification checkbox has been operated on the setting window. This boot completion notification checkbox will be described in detail later with reference to FIG. 13. If the boot completion notification checkbox has been operated, the process goes on to step S32. Otherwise, the process goes on to step S35.

(Step S32) The input reception unit 116 determines whether the boot completion notification checkbox is ON (checked). If the boot completion notification checkbox is ON, the process goes on to step S33. If the boot completion notification checkbox is OFF, the process goes on to step S34.

(Step S33) The input reception unit 116 sets a boot completion notification flag to ON. Then, the process goes on to step S12 (described earlier with reference to FIG. 5). This boot completion notification flag is a flag that indicates whether to make a boot completion notification, i.e., whether to execute the boot completion notification process during boot-up of the information processing apparatus 100, and is stored in the RAM 102, as will be described in detail later with reference to FIG. 11.

(Step S34) The input reception unit 116 sets the boot completion notification flag to OFF. Then, the process goes on to step S12 (described earlier with reference to FIG. 5).

In this embodiment, similarly to step S14, in these steps S33 and S34, the update of the boot completion notification flag based on the user operation made on the boot completion notification checkbox is not actually done, but only an update instruction to update the boot completion notification flag and the contents of the update are stored in the RAM 102. The update is actually done at step S44, as will be described later with reference to FIG. 8. That is to say, before step S44 is executed, it is possible to cancel this update by canceling the update instruction at step S46 to be described later with reference to FIG. 8, which results in canceling the setting process of this time with keeping the current setting.

(Step S35) The input reception unit 116 determines whether a measurement value button has been pressed on the setting window. This measurement value button will be described in detail later with reference to FIG. 13. If the measurement value setting button has been pressed, the process goes on to step S36. Otherwise, the process goes on to step S41 (to be described in detail later with reference to FIG. 8).

(Step S36) The input reception unit 116 sets the stopwatch flag to ON. Then, the process goes on to step S12 (described earlier with reference to FIG. 5).

In this embodiment, similarly to step S14, in this step S36, the update of the stopwatch flag based on the user operation made on the measurement value button is not actually done, but only an update instruction to update the stopwatch flag and the contents of the update are stored in the RAM 102. This update is actually done at step S44, as will be described later with reference to FIG. 8. That is to say, before step S44 is executed, it is possible to cancel this update by canceling the update instruction at step S46 to be described later with reference to FIG. 8, which results in canceling the setting process of this time with keeping the current setting.

(Step S41) The input reception unit 116 determines whether the scrollbar has been operated on the setting window. This scrollbar will be described in detail later with reference to FIG. 13. If the scrollbar has been operated, the process goes on to step S42. Otherwise, the process goes on to step S43.

(Step S42) The input reception unit 116 sets the position of the scrollbar displayed on the setting window and a value pointed by the scrollbar. Then, the process goes on to step S12 (described earlier with reference to FIG. 5).

(Step S43) The input reception unit 116 determines whether an OK button has been pressed on the setting window. This OK button will be described in detail later with reference to FIG. 13. If the OK button has been pressed, the process goes on to step S44. Otherwise, the process goes on to step S45.

(Step S44) The update unit 115 updates the boot completion notification timing table 151a, boot-up detection flag, boot completion notification flag, and stopwatch flag according to the setting contents changed by this setting process, on the basis of the update instructions and the contents of the updates stored in the RAM 102, and reflects the changes in the setting. Then, the process is completed.

(Step S45) The input reception unit 116 determines whether a cancel button has been pressed on the setting window. This cancel button will be described in detail later with reference to FIG. 13. If the cancel button has been pressed, the process goes on to step S46. Otherwise, the process goes on to step S12 (described earlier with reference to FIG. 5).

(Step S46) The update unit 115 deletes the update instructions and the contents of the updates from the RAM 102. That is, the update unit 115 does not update the boot completion notification timing table 151a, boot-up detection flag, boot completion notification flag, or stopwatch flag. Then, the process is completed.

Figure 9:
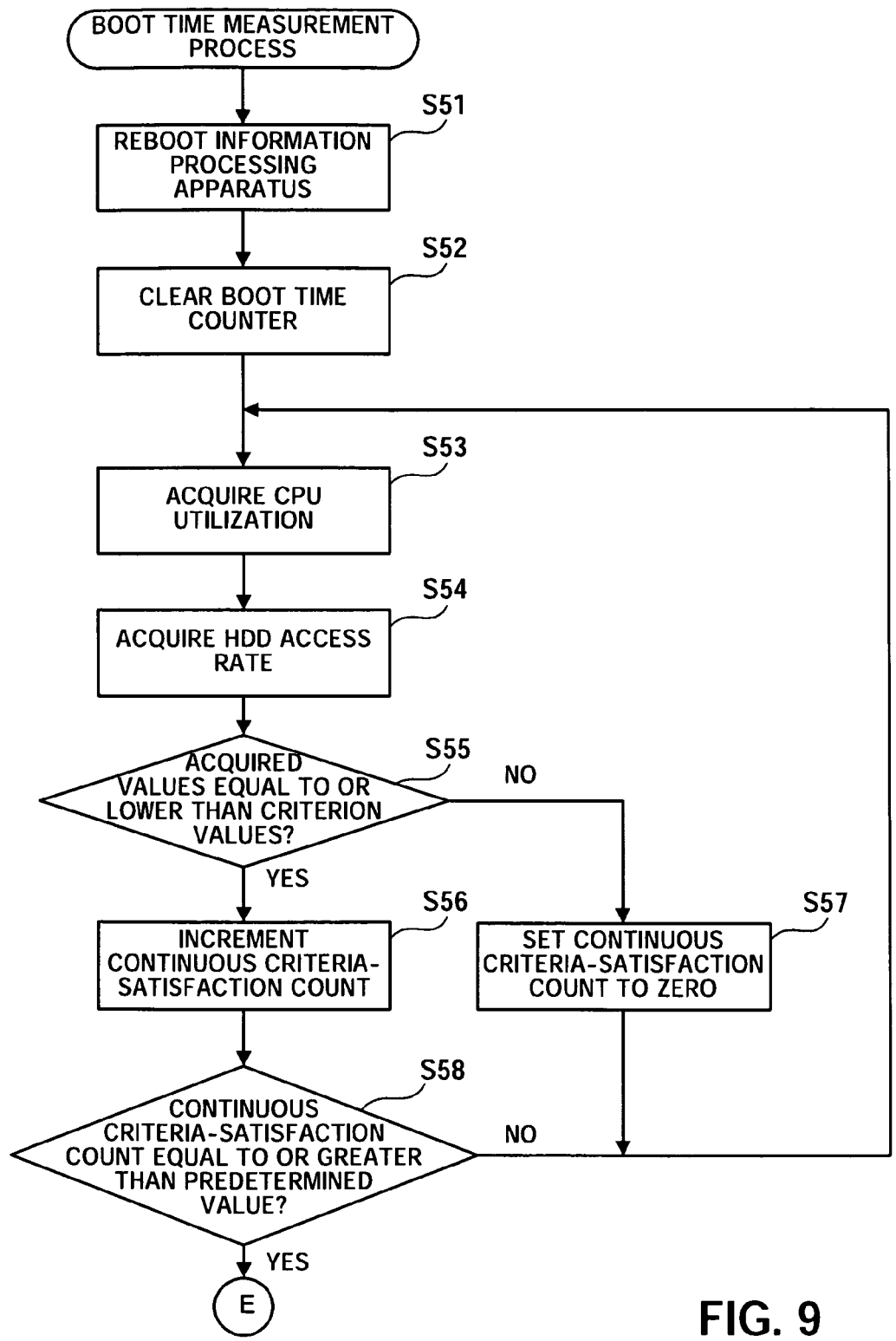
FIG. 9 is a flowchart of a boot time measurement process.
Figure 10:
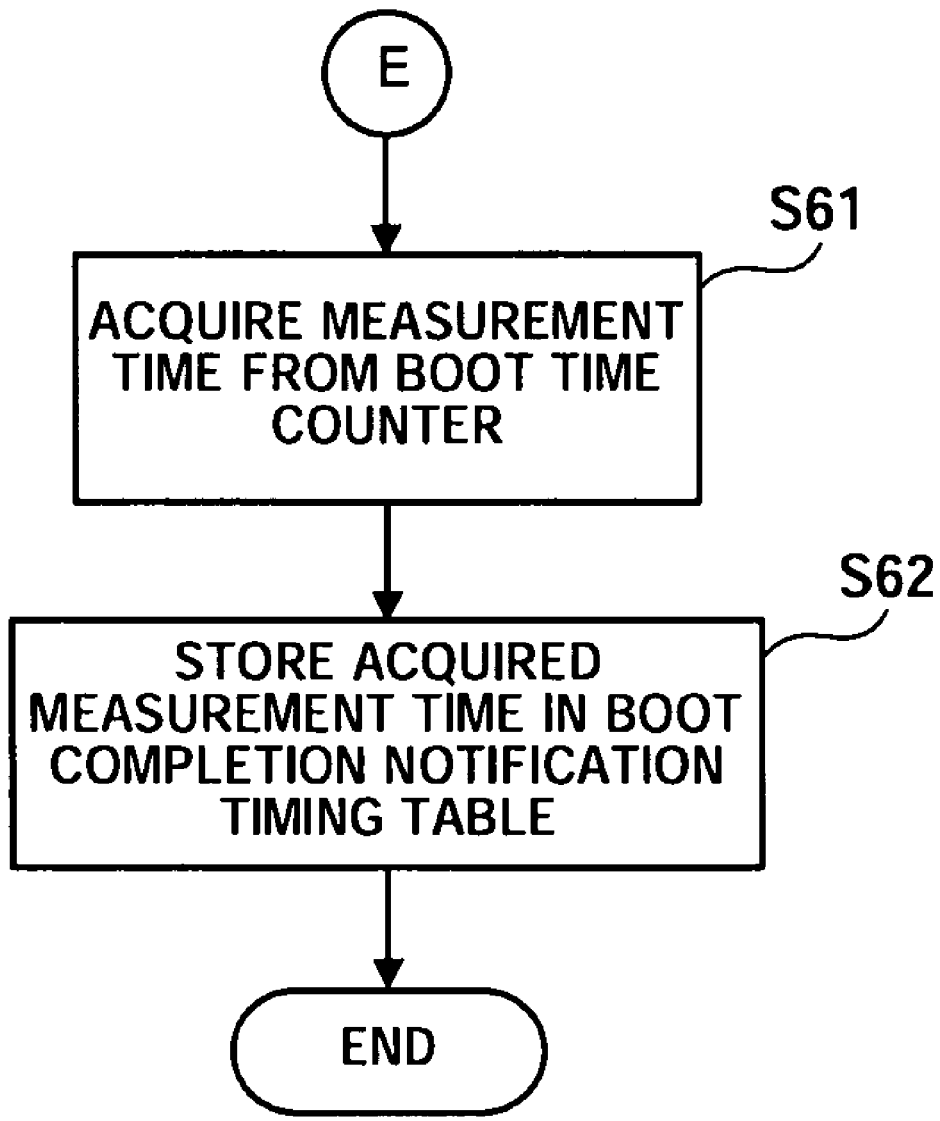
FIG. 10 is the flowchart of the boot time measurement process.

FIGS. 9 and 10 are a flowchart of a boot time measurement process. The boot time measurement process of FIGS. 9 and 10 is a process that is executed to measure a boot time at step S22 (described earlier with reference to FIG. 6) of the setting process (described earlier with reference to FIGS. 5 to 8). This boot time measurement process is initiated by a user pressing the boot time measurement button (described later with reference to FIG. 13) in the setting process.

(Step S51) The determination unit 112 reboots the information processing apparatus 100. Then, a time taken for the reboot is measured with the boot time measurement process of this embodiment. This measured time is used for determining a value of boot completion notification timing. To initiate the boot time measurement process, a boot time measurement instruction, which causes the information processing apparatus 100 to execute step S52 and subsequent steps of the boot time measurement process immediately after the reboot begins, is stored in the HDD 103 before the reboot begins at step S51. Thereby, when the information processing apparatus 100 begins to reboot, step S52 and subsequent steps also begin to execute.

(Step S52) The stopwatch unit 111 clears (resets) a boot time counter when detecting the reboot of the information processing apparatus 100. This boot time counter is a stopwatch that is provided in the CPU 101 to measure a time elapsed after the stopwatch unit 11 detects boot-up (including reboot, hereinafter, the same applies) of the information processing apparatus 100 until the determination unit 112 detects completion of the boot-up of the information processing apparatus 100. The boot time counter is also used to measure a time elapsed after the stopwatch unit 111 detects the boot-up, in order to determine whether the time reaches boot completion notification timing, as will be described in detail later with reference to FIG. 11.

(Step S53) The acquisition unit 114 acquires the utilization of the CPU 101 in the information processing apparatus 100. This utilization of the CPU 101 is used as an evaluation value to indicate the load imposed on the information processing apparatus 100 on boot-up. The utilization of the CPU 101 is acquired with API (Application Program Interface).

(Step S54) The acquisition unit 114 acquires a rate of access to the HDD 103 in the information processing apparatus 100. This rate of access to the HDD 103 indicates an amount of data read and written on the HDD 103 within a predetermined time period, and is used as an evaluation value to indicate the load imposed on the information processing apparatus 100 on boot-up, similarly to the utilization of the CPU 101. This rate of access to the HDD 103 is acquired with the API.

This embodiment employs the utilization of the CPU 101 and the rate of access to the HDD 103 to evaluate the load imposed on the information processing apparatus 100 on boot-up. Other than these, the utilization of the RAM 102 indicating how much the RAM 102 is being used, the size of page file usage, or any other value may be used as long as they indicate the load on the information processing apparatus 100. In addition, a combination of some of them or a combination of all of them may be used.

(Step S55) The determination unit 112 determines whether or not both of the utilization of the CPU 101 acquired by the acquisition unit 114 at step S53 and the rate of access to the HDD 103 acquired at step S54 are equal to or lower than predetermined criterion values. If both of these acquired values are equal to or lower than the criterion values, the process goes on to step S56. If at least one of them exceeds the criterion value, the process goes on to step S57. The criterion values are independently set for the utilization of the CPU 101 and the rate of access to the HDD 103. Further, the criterion values are low enough to determine that load conditions of the information processing apparatus 100 are low.

According to the embodiment, the determination unit 112 determines whether or not both of the utilization of the CPU 101 and the rate of access to the HDD 103 are equal to or lower than the respective criterion values. Alternatively, it may be determined whether or not at least one of the acquired values is equal to or lower than a criterion value. In addition, the determination unit 112 may unify the utilization of the CPU 101 and the rate of access to the HDD 103 to obtain a unified evaluation value in order to evaluate the load on the information processing apparatus 100 holistically. Further, other than these, the utilization of the RAM 102 indicating how much the RAM 102 is being used, the size of page file usage, or any other value may be used as long as they indicate the load on the information processing apparatus 100. In addition, a combination of some of them or a combination of all of them may be used.

(Step S56) The determination unit 112 increments the count of a continuous criteria-satisfaction (achievement) counter stored in the RAM 102 by one. This continuous criteria-satisfaction counter is a counter that indicates how many times in a row acquired values indicating load are equal to or lower than the respective criterion values. In other words, the number of times of continuously determining at step S55 that acquired values are equal to or lower than the criterion values is counted.

(Step S57) The determination unit 112 clears the count of the continuous criteria-satisfaction counter stored in the RAM 102 (by substituting the count with 0). As a result, the continuous criteria-satisfaction counter is reset when it is determined at step S55 that any acquired value exceeds the criterion value. Then, the process proceeds to step S53.

(Step S58) The determination unit 112 determines whether the continuous criteria-satisfaction count is equal to or greater than a predetermined value. If the continuous criteria-satisfaction count is equal to or greater than the predetermined value, the process proceeds to step S61 (which will be described later with reference to FIG. 10). Otherwise, the process proceeds to step S53. The determination unit 112 takes and uses the count of the continuous criteria-satisfaction counter stored in the RAM 102 as the continuous criteria-satisfaction count in this determination. The predetermined value indicates how many times in a row the load conditions of the information processing apparatus 100 need to be determined to be low in order to determine that the boot-up of the information processing apparatus 100 is complete.

(Step S61) The stopwatch unit 111 acquires a measurement time from the boot time counter. That is, the determination unit 112 acquires the boot time when it is determined that the continuous criteria-satisfaction count has reached the predetermined value.

(Step S62) The update unit 115 updates the boot completion notification timing table 151a (described earlier with reference to FIG. 4) to store the measurement time acquired at step S61. If the maximum number (for example, 15 pieces) of data is stored, the oldest data is deleted and this newly acquired data is stored.

Figure 11:
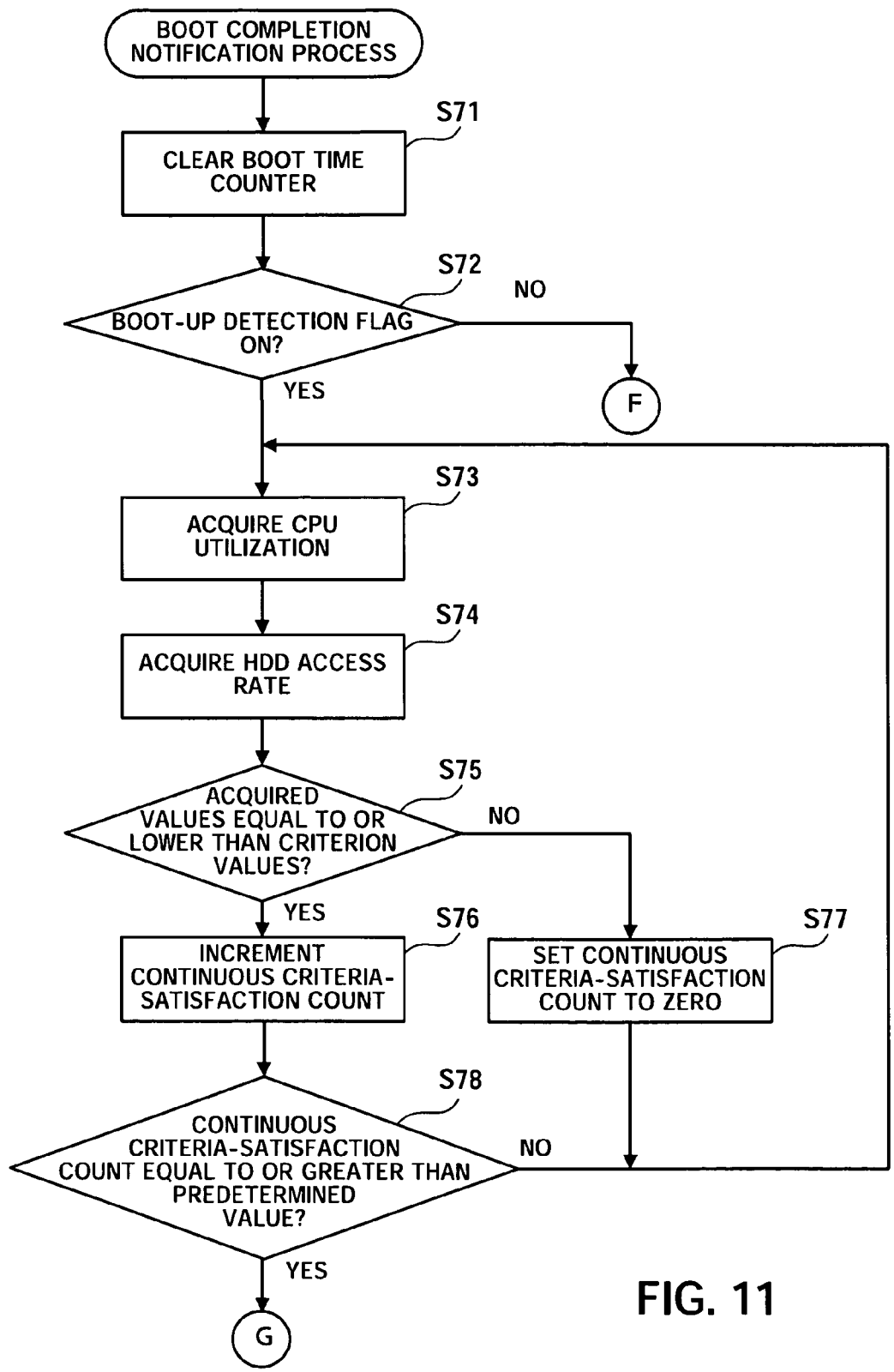
FIG. 11 is a flowchart of a boot completion notification process.
Figure 12:
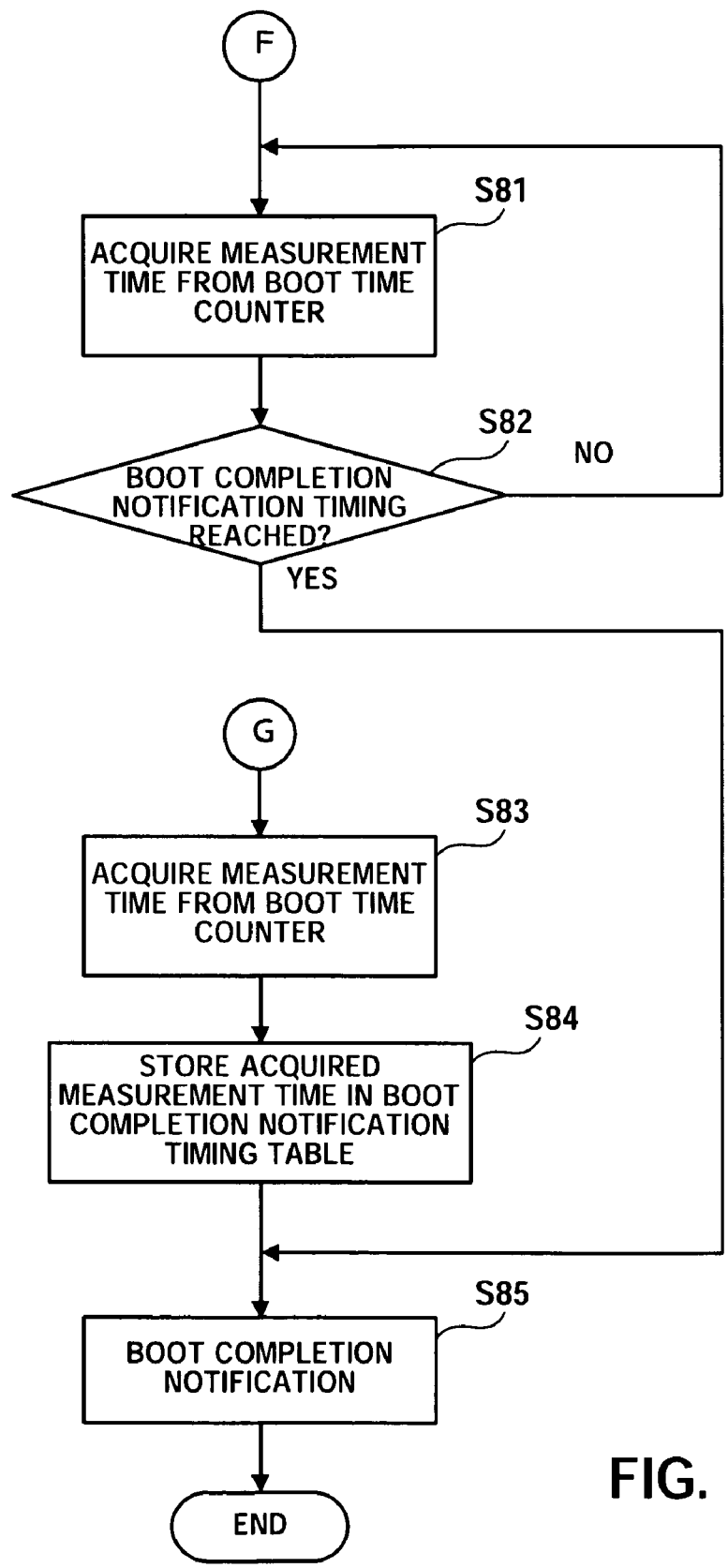
FIG. 12 is the flowchart of the boot completion notification process.

FIGS. 11 and 12 are a flowchart of a boot completion notification process. When the information processing apparatus 100 confirms at the time of boot-up that the boot completion notification flag (described earlier with reference to FIG. 7) stored in the RAM 102 is ON, this boot completion notification process illustrated in FIGS. 11 and 12 is initiated in order to make a boot completion notification.

(Step S71) When boot-up of the information processing apparatus 100 is detected, the stopwatch unit 111 clears the boot time counter. This boot time counter is used to measure the time elapsed from the detection of the boot-up for use in determination on whether this time reaches boot completion notification timing. As a method of detecting the beginning of the boot-up of the information processing apparatus 100, it may be so designed that this step S71 is executed as early as possible in the boot-up process of the information processing apparatus 100.

(Step S72) The determination unit 112 determines whether the boot-up detection flag (described earlier with reference to FIG. 6) stored in the RAM 102 is ON. If the boot-up detection flag is ON, the process goes on to step S73. If the boot-up detection flag is OFF, the process goes on to step S81 (described later with reference to FIG. 12).

(Step S73) The acquisition unit 114 acquires the utilization of the CPU 101 of the information processing apparatus 100. This utilization of the CPU 101 is used as an evaluation value to indicate the load imposed on the information processing apparatus 100 on boot-up, as in the boot time measurement process (described earlier with reference to FIGS. 9 and 10).

(Step S74) The acquisition unit 114 acquires a rate of access to the HDD 103 of the information processing apparatus 100. This rate of access to the HDD 103 indicates an amount of data read and written on the HDD 103 within a predetermined time period, and is used as an evaluation value to indicate the load imposed on the information processing apparatus 100 on boot-up, as in the boot time measurement process (described earlier with reference to FIGS. 9 and 10).

This embodiment employs the utilization of the CPU 101 and the rate of access to the HDD 103 to evaluate the load imposed on the information processing apparatus 100 on boot-up. Other than these, the utilization of the RAM 102 indicating how much the RAM 102 is being used, the size of page file usage, or any other value may be used as long as they indicate the load on the information processing apparatus 100, as in the boot time measurement process. In addition, a combination of some of them or a combination of all of them may be used.

(Step S75) The determination unit 112 determines whether or not both of the utilization of the CPU 101 acquired by the acquisition unit 114 at step S73 and the rate of access to the HDD 103 acquired at the step S74 are equal to or lower than predetermined criterion values. If both of the acquired values are equal to or lower than the criterion values, the process goes on to step S76. If at least one of the acquired values exceeds the criterion value, the process goes on to step S77. Similarly to the boot time measurement process, the criterion values are independently set for the utilization of the CPU 101 and the rate of access to the HDD 103. In addition, the criterion values are low enough to determine that the load conditions of the information processing apparatus 100 on boot-up are low.

In this connection, according to this embodiment, the determination unit 112 determines whether both of the utilization of the CPU 101 and the rate of access to the HDD 103 are equal to or lower than the respective criterion values, as in the boot time measurement process. Alternatively, it may be determined whether or not at least one of the acquired values is equal to or lower than a criterion value. In addition, the determination unit 112 may unify the utilization of the CPU 101 and the HDD 103 to obtain a unified evaluation value in order to evaluate the load on the information processing apparatus 100 holistically. Furthermore, for this determination, the determination unit 112 may use the utilization of the RAM 102 indicating how much the RAM 102 is being used, the size of page file usage, or any other value as long as they indicate the load on the information processing apparatus 100. In addition, a combination of some of them or a combination of all of them may be used for the determination.

(Step S76) The determination unit 112 increments the count of the continuous criteria-satisfaction counter stored in the RAM 102. That is, the number of times of determining at step S75 that acquired values are equal to or lower than the criterion values is counted.

(Step S77) The determination unit 112 clears the count of the continuous criteria-satisfaction counter stored in the RAM 102 (by substituting the count with 0). That is, the continuous criteria-satisfaction count is reset when it is determined at step S75 that any acquired value exceeds the criterion value. Then, the process proceeds to step S73.

(Step S78) The determination unit 112 determines whether or not the continuous criteria-satisfaction count is equal to or greater than a predetermined value. If this continuous criteria-satisfaction count is equal to or greater than the predetermined value, the process proceeds to step S83 (to be described later with reference to FIG. 12). Otherwise, the process proceeds to step S73. The determination unit 112 takes and uses the count of the continuous criteria-satisfaction counter stored in the RAM 102 as the continuous criteria-satisfaction count in this determination, as in the boot time measurement process. The predetermined value is set to indicate how many times in a row the load conditions of the information processing apparatus 100 on boot-up need to be determined to be low in order to determine that the boot-up of the information processing apparatus 100 is complete.

(Step S81) The stopwatch unit 111 acquires the measurement time from the boot time counter. That is, the stopwatch unit 111 uses the boot time counter to measure the boot time of the information processing apparatus 100.

(Step S82) The determination unit 112 determines whether the boot time measured by the stopwatch unit 111 has reached the boot completion notification timing for making a boot completion notification. If this boot time has reached the boot completion notification timing, the process proceeds to step S85. Otherwise, the process proceeds to step S81. This boot completion notification timing is a value indicating timing for making a boot completion notification, and is taken from when the stopwatch unit 111 detects the beginning of boot-up of the information processing apparatus 100. As the boot completion notification timing, a value set by a user in the setting process (described earlier with reference to FIGS. 5 to 8) or an average value of measurement times (described earlier with reference to FIG. 4) measured in the boot time measurement process is used.

(Step S83) The stopwatch unit 111 acquires the measurement time from the boot time counter. Thereby, the boot time until the determination unit 112 determines that the continuous criteria-satisfaction count is equal to or greater than the predetermined value is measured.

(Step S84) The update unit 115 updates the boot completion notification timing table 151a (described earlier with reference to FIG. 4) to store the measurement time acquired at step S83. If the maximum number (for example, 15 pieces) of data is stored, the oldest data is deleted and the newly obtained data is stored.

(Step S85) The output unit 113 outputs a boot completion notification. More specifically, the output unit 113 outputs boot completion notification display information for displaying a boot completion notification window (described later with reference to FIG. 14) on the display screen of the monitor 11. Thereby, the boot completion notification window is displayed on the monitor 11, so as to notify the user that the information processing apparatus 100 has completed its boot-up.

The following describes what to display on a screen according to the embodiment.

Figure 13:
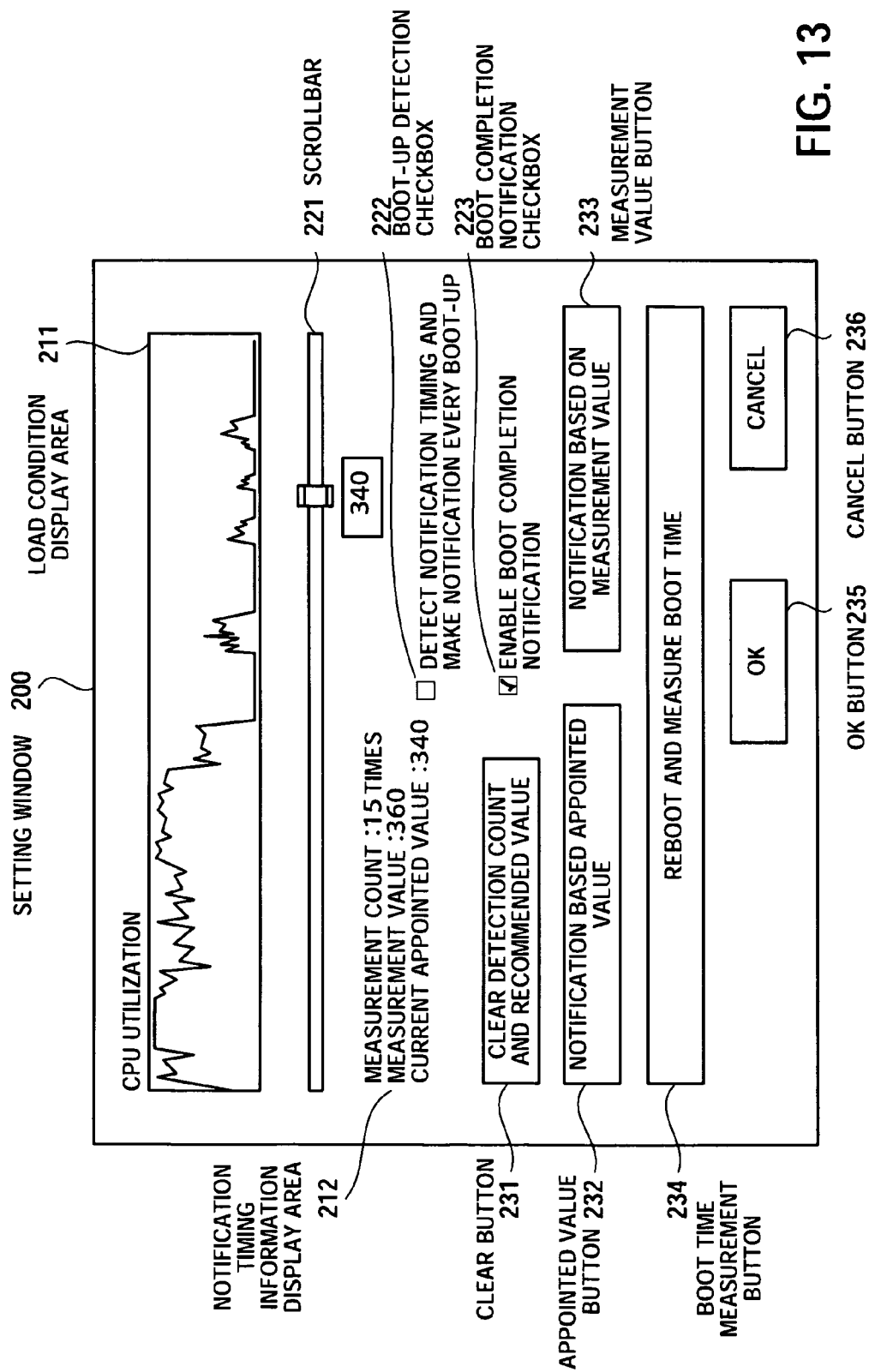
FIG. 13 illustrates a setting window.

FIG. 13 illustrates a setting window. The setting window 200 illustrated in FIG. 13 is a window that is displayed on a screen of the monitor 11 connected to the information processing apparatus 100.

The setting window 200 has a load condition display area 211, a notification timing information display area 212, a scrollbar 221, a boot-up detection checkbox 222, a boot completion notification checkbox 223, a clear button 231, an appointed value button 232, a measurement value button 233, a boot time measurement button 234, an OK button 235, and a cancel button 236.

The load condition display area 211 is an area for displaying a graph that represents a change in load imposed on the information processing apparatus 100 during boot-up. In the setting window 200 of FIG. 13, the load condition display area 211 displays a graph that represents a change in the CPU utilization as the utilization of the CPU 101. On the basis of this graph displayed in the load condition display area 221, the user is able to set an appointed time so as to make a boot completion notification when the load conditions of the information processing apparatus 100 on boot-up become low.

The setting window 200 of FIG. 13 displays a graph representing a change in the CPU utilization. This graph may be switched to some other graph representing a load condition, such as a graph representing a change in the HDD access rate that is the rate of access to the HDD 103 (not illustrated). This embodiment displays such load condition graphs one by one. Alternatively, a plurality of graphs may be displayed at the same time.

The notification timing information display area 212 displays information of the boot completion notification timing information stored in the boot completion notification timing table 151a (described earlier with reference to FIG. 4). The information displayed in the notification timing information display area 212 includes "measurement count" indicating how many times the measurement time (described earlier with reference to FIG. 4) was obtained with the boot time measurement process (described earlier with reference to FIGS. 9 and 10), "measurement value" that is a value of notification timing calculated based on the measurement times obtained with the boot time measurement process, and "current appointed value" indicating the appointed time (described earlier with reference to FIG. 4) set by the user.

The scrollbar 221 is a scrollbar that receives user operation regarding an appointed time (described earlier with reference to FIGS. 5 to 8). By a user selecting an appointed time as notification timing for a boot completion notification, the boot completion notification is made in the boot completion notification process (described earlier with reference to FIGS. 11 and 12) on the basis of the appointed time set via the scrollbar 221.

The boot-up detection checkbox 222 is a checkbox for setting whether to acquire the load conditions of the information processing apparatus 100 on boot-up or compare a time elapsed from detection of the beginning of the boot-up process and the boot completion notification timing information stored in the boot completion notification timing table 151a, to detect the boot completion of the information processing apparatus 100 and then output a boot completion notification. To detect notification timing every boot-up, the user checks the boot-up detection checkbox 222. On the other hand, to obtain and use the notification timing from the boot completion notification timing table 151a, the user unchecks the boot-up detection checkbox 222.

If the load conditions are expected to change in boot-up immediately after the information processing apparatus 100 is newly introduced, immediately after a resident application or an application to be loaded in boot-up is changed, or in some other situation, which causes insufficient collection of new load conditions, the user checks the boot-up detection checkbox 222 to detect the notification timing on the basis of the load in order to make the boot completion notification.

The boot completion notification checkbox 223 is a checkbox for setting whether to perform the boot completion notification process during the boot-up of the information processing apparatus 100. To perform the boot completion notification process in order to make a boot completion notification, the user checks this boot completion notification checkbox 223. To disable the boot completion notification process so as not to make a boot completion notification, the user unchecks the boot completion notification checkbox 223.

The clear button 231 is a button for deleting all measurement times obtained with the boot time measurement process from the boot completion notification timing table 151a and the measurement count of the boot times. To delete the all measurement times from the boot completion notification timing table 151a and also clear the measurement count, the user presses this clear button 231.

If the load conditions are expected to change in boot-up immediately after the information processing apparatus 100 is newly introduced, immediately after a resident application or an application to be loaded in boot-up is changed, or in some other situation, the user presses this clear button 231 to eliminate the effects of the load conditions collected before the change.

The appointed value button 232 is a button for setting the stopwatch flag to OFF so that the value of the notification timing set by the user with the scrollbar 221 is stored as an appointed time in the boot completion notification timing table 151a and the boot completion notification is made on the basis of the appointed time that is the value set by the user as notification timing. To make a boot completion notification based on the notification timing set by the user, the user presses this appointed value button 232.

The measurement value button 233 is a button for setting the stopwatch flag to ON so that the boot completion notification is made on the basis of the measurement times obtained with the boot time measurement process. To make a boot completion notification on the basis of the notification timing calculated by averaging the measurement times, the user presses this measurement value button 233.

The boot time measurement button 234 is a button for performing the boot time measurement process. By the user pressing this boot time measurement button 234, the information processing apparatus 100 is rebooted immediately to measure a boot time.

The OK button 235 is a button for fixing and reflecting the changes in the setting made on the setting window 200 in the boot completion notification timing table 151a, boot-up detection flag, boot completion notification flag, and stopwatch flag. To fix and reflect the setting changes made on the setting window 200, the user presses the OK button 235.

The cancel button 236 is a button for canceling the changes in the setting made on the setting window 200 so as not to reflect them in the boot completion notification timing table 151a, boot-up detection flag, boot completion notification flag, or stopwatch flag. To cancel the setting changes made on the setting window 200, the user presses the cancel button 236.

FIG. 14 illustrates a boot completion notification window. The boot completion notification window 300 illustrated in FIG. 14 is a window that is displayed on a screen of the monitor 11 connected to the information processing apparatus 100.

The boot completion notification window 300 includes a boot complete message 301 and an OK button 302. This boot completion notification window 300 is a window that displays the boot complete message 301 to make a notification that the boot-up of the information processing apparatus 100 has completed.

The boot complete message 301 is a message for making a notification that the boot completion notification process (described earlier with reference to FIGS. 11 and 12) has determined that the boot-up of the information processing apparatus 100 is complete. This boot complete message 301 allows the user to confirm that the information processing apparatus 100 has completed its boot-up and now runs stable.

The OK button 302 is a button for closing the boot completion notification window 300. After confirming the boot complete message 301, the user presses this OK button 302 to close the boot completion notification window 300, so that the user starts to use the information processing apparatus 100 which has completed its boot-up.

In general, high load is imposed on a CPU during boot-up of an information processing apparatus such as a PC. Even after the startup of the OS of the information processing apparatus is completed, the startup of other applications and services may still be in progress. Therefore, the high load on the CPU and so on in the information processing apparatus do not decrease until the startup of them is also completed.

According to this embodiment, data indicating the load conditions of the information processing apparatus 100 on boot-up is collected and analyzed to calculate boot completion notification timing for outputting a boot completion notification. This makes it possible to make a boot completion notification at appropriate timing even when a change in applications causes a change in load of the boot-up process.

In addition, according to the embodiment, the setting window provides the user with recommended timing for determining that boot-up is completed after the boot-up begins. If the user desires to use the boot completion notification timing recommended on the setting window, the user enables the boot completion notification function and presses the OK button only, thereby completing the setting.

Further, when a time elapsed after the beginning of boot-up of the information processing apparatus 100 is detected reaches the notification timing set by the user, the boot completion notification is displayed on the screen of the monitor 11.

As described above, according to the embodiment, the stopwatch unit 111 acquires a time elapsed from the beginning of boot-up of the information processing apparatus 100 until when the information processing apparatus 100 becomes stable with low load. At the next boot-up of the information processing apparatus 100, the determination unit 112 compares a time elapsed from the beginning of the boot-up, measured by the stopwatch unit 111, with the time that was acquired last and is listed in the boot completion notification timing table 151a to determine the completion of the boot-up, and then the output unit 113 notifies the user that the information processing apparatus 100 has completed its boot-up.

As described above, the embodiment makes it possible to notify the user of boot completion of the information processing apparatus 100 on the basis of the load conditions of the information processing apparatus 100 on boot-up. Therefore, the user is able to know whether the information processing apparatus 100 has completed its boot-up or not. Since the user is able to confirm that the information processing apparatus 100 has completed its boot-up, runs stable, and is now ready to use, the user is able to start to use the information processing apparatus 100 comfortably after the boot-up.

In addition, it is possible to prevent the user from using the information processing apparatus 100 which now boots up under high load. The user is able to know the timing when the information processing apparatus 100 runs stable. Therefore, the user is able to start to use the information processing apparatus 100 comfortably after the boot-up.

In addition, the completion of boot-up of the information processing apparatus 100 is determined on the basis of a change in the load conditions of the information processing apparatus 100 on boot-up. Therefore, as compared with the case of making a boot completion notification in conjunction with the completion of startup of a specified OS or program such as an application, this embodiment makes it possible to cope with a change in startup of applications in order to make a boot completion notification at appropriate notification timing even in the case where an OS is a multitasking OS that does not have a fixed sequence of startup completion of the applications.

In addition, even when the user installs a new application or deletes an application, it is possible to cope with the change influencing the boot-up process of the information processing apparatus 100.

The processing functions described above can be realized by a general computer. In this case, a program is prepared, which describes processes for the functions of the information processing apparatus 100. The program is executed by a computer, whereupon the aforementioned processing functions are accomplished by the computer.

The program describing the processes may be recorded on a computer-readable recording medium. Computer-readable recording media include magnetic recording devices, optical discs, magneto-optical recording media, semiconductor memories, etc. The magnetic recording devices include HDDs, Flexible Disks (FD), magnetic tapes (MT), etc. The optical discs include DVDs (Digital Versatile Discs), DVD-RAMs, CD-ROMs (Compact Disc-Read Only Memory), CD-R (Recordable)/RW (ReWritable), etc. The magneto-optical recording media include MOs (Magneto-Optical disk) etc.

To distribute the program, portable recording media, such as DVDs and CD-ROMs, on which the program is recorded may be put on sale. Alternatively, the program may be stored in the storage device of a server computer and may be transferred from the server computer to other computers through a network.

A computer which is to execute the program stores in its storage device the program recorded on a portable recording medium or transferred from the server computer, for example. Then, the computer runs the program. The computer may run the program directly from the portable recording medium. Also, while receiving the program being transferred from the server computer, the computer may sequentially run this program.

The disclosed information processing apparatus and boot completion notification program make it possible to notify a user of boot completion of the information processing apparatus, on the basis of the load conditions of the information processing apparatus on boot-up.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that various changes, substitutions, and alterations could be made hereto without departing from the spirit and scope of the invention.

What is claimed is:

1. An information processing apparatus comprising:
  a storage unit that stores boot completion notification timing information indicating notification timing for making a boot completion notification that notifies a user that the information processing apparatus has completed boot-up and is now ready to use;
  a stopwatch unit that detects the boot-up of the information processing apparatus, and measures as a boot time a time elapsed from the detection of the boot-up;
  a determination unit that determines whether the boot time measured by the stopwatch unit has reached the notification timing indicated by the boot completion notification timing information;
  an output unit that outputs the boot completion notification when the determination unit determines that the boot time has reached the notification timing;
  an acquisition unit that acquires load conditions of the information processing apparatus on boot-up; and
  an update unit that updates the boot completion notification timing information stored in the storage unit,
  wherein the determination unit determines on the basis of the load conditions acquired by the acquisition unit whether the information processing apparatus has completed the boot-up,
  wherein the update unit acquires from the stopwatch unit the boot time, which indicates when the information processing apparatus completed the boot-up, when the determination unit determines that the information processing apparatus has completed the boot-up, and stores the acquired boot time as the boot completion notification timing information in the storage unit.

2. An information processing apparatus comprising:
an storage unit that stores boot completion notification timing information indicating notification timing for making a boot completion notification that notifies a user that the information processing apparatus has completed boot-up and is now ready to use;
a stopwatch unit that detects the boot-up of the information processing apparatus, and measures as a boot time a time elapsed from the detection of the boot-up;
an acquisition unit that acquires load conditions in the boot-up of the information processing apparatus;
a determination unit that determines on the basis of the load conditions acquired by the acquisition unit whether the information processing apparatus has completed the boot-up; and
an output unit that outputs the boot completion notification when the determination unit determines that the information processing apparatus has completed the boot-up.

3. The information processing apparatus according to claim 2, further comprising:
an update unit that updates the boot completion notification timing information stored in the storage unit, by acquiring from the stopwatch unit the boot time, which indicates when the information processing apparatus completed the boot-up, when the determination unit determines that the information processing apparatus has completed the boot-up, and storing the acquired boot time as the boot completion notification timing information in the storage unit.

4. The information processing apparatus according to claim 2, wherein the acquisition unit acquires utilization of a CPU of the information processing apparatus as the load conditions.

5. The information processing apparatus according to claim 2, wherein the acquisition unit acquires a rate of access to an HDD of the information processing apparatus as the load conditions.

6. The information processing apparatus according to claim 2, wherein:
the boot completion notification timing information includes appointed timing information that, indicates the notification timing set by a user; and
the information processing apparatus further comprises an input reception unit that receives the appointed timing information set by the user.

7. The information processing apparatus according to claim 2, wherein the determination unit determines that the information processing apparatus has completed the boot-up when a value indicating the load conditions acquired by the acquisition unit is equal to or lower than a predetermined value.

8. The information processing apparatus according to claim 2, wherein the determination unit repeats the determination on whether the load conditions acquired by the acquisition unit satisfy predetermined criteria, and determines that the information processing apparatus has completed the boot-up when a result of the determination that the load conditions satisfy the predetermined criteria is obtained a predetermined number of times in a row.

9. The information processing apparatus according to claim 8, wherein the determination unit determines that the predetermined criteria are satisfied when a value indicating the load conditions acquired by the acquisition unit is equal to or lower than a predetermined value.

10. A non-transitory computer-readable medium storing a boot completion notification program causing a computer to operate as:
a storage unit that stores boot completion notification timing information indicating notification timing for making a boot completion notification that notifies a user that an information processing apparatus has completed boot-up and is now ready to use;
a stopwatch unit that detects boot-up of the information processing apparatus, and measures as a boot time a time elapsed from the detection of the boot-up;
an acquisition unit that acquires load conditions in the boot-up of the information processing apparatus;
a determination unit that determines on a basis of the load conditions acquired by the acquisition unit whether the information processing apparatus has completed the boot-up; and
an output unit that outputs the boot completion notification when the determination unit determines that the information processing apparatus has completed the boot-up.

* * * * *